US00PP18716P2

(12) United States Plant Patent
Austin

(10) Patent No.: US PP18,716 P2
(45) Date of Patent: Apr. 8, 2008

(54) SHRUB ROSE PLANT NAMED 'AUSRIMINI'

(50) Latin Name: *Rosa hybrida*
Varietal Denomination: AUSrimini

(75) Inventor: David C. H. Austin, Wolverhampton (GB)

(73) Assignee: David Austin Roses Limited, Albrighton, Wolverhampton (GB)

( * ) Notice: Subject to any disclaimer, the term of this patent is extended or adjusted under 35 U.S.C. 154(b) by 0 days.

(21) Appl. No.: 11/635,214

(22) Filed: Dec. 6, 2006

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

A new and distinct variety of shrub rose plant substantially as herein shown and described, characterized particularly by its medium sized, cupped rosettes of pure mid-pink blossoms; having a very strong myrrh fragrance; and its tall, slightly arching growth with dark, glossy foliage.

1 Drawing Sheet

Genus and species: *Rosa hybrida.*
Variety denomination: 'AUSrimini'.

ORIGIN OF THE INVENTION

The present invention relates to a new and distinct variety of a shrub rose plant named 'AUSrimini' which was originated by me by crossing an unnamed, unpatented seedling with an unnamed, unpatented seedling.

BACKGROUND OF THE INVENTION

The primary objective of this breeding was to produce a repeat flowering healthy variety with rose pink blooms having a strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Medium sized, cupped rosettes of pure mid-pink color.
2. A very strong myrrh fragrance.
3. Tall, slightly arching growth with dark, glossy foliage.

Asexual reproduction of this new variety by budding, as performed at Albrighton, England, shows that the foregoing and all other characteristics and distinctions come true to form and are established and transmitted through succeeding propagations.

Comparison with Parents

The seed parent has semi-double blooms compared to the full, double blooms of 'AUSrimini' and the latter has smaller leaves. The pollen parent has taller growth and copper colored blooms compared with the pink blooms of 'AUSrimini'.

Comparison with Similar Variety

'AUSmak' (U.S. Plant Pat. No. 9,526) has more petals per bloom than 'AUSrimini' and less upright growth. 'AUSrimini' has glossier foliage and a hint of apricot on its pale pink blooms, which 'AUSmak' does not have.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants commencing at one year of age grown in a garden environment at Albrighton, England.

Blooming habit: Recurrent. The number of blooms per plant during the growing season is profuse; there are too many to count.

Bud:
*Size.*—About 3–3.5 cm long and 1.7 cm in diameter when the petals start to unfurl.
*Form.*—The bud form is pointed ovoid.
*Color.*—When sepals first divide, bud color is Red Group 50A. When half blown, the upper sides of the petals are Red Group 56C top half of petal and Red Group 37C basal half and the lower sides of the petals are Red Group 56C top half of petal and Orange-Red Group 31D basal half.

*Sepals.*—Color: Upper surface: Yellow-Green Group 144A with Yellow-Green Group 145C at base and overlaid with Greyed-Red Group 181B. Lower surface: Yellow-Green Group 144A with Yellow-Green Group 144C at base and irregular spots of Greyed-Red Group 181B. Length: 2.5 cm. Width: 0.9–1.0 cm. Shape: Subulate. Surface texture: Upper surface: Pubescent. Lower surface: Smooth. There are three lightly appendaged sepals. There are two unappendaged sepals with canescent edges. (Occasionally, there are only four sepals (two appendaged and two unappendaged).

*Receptacle.*—Color: Green Group 143B. Shape: Campanulate. Size: Medium, about 1.0 cm long×1.0 cm wide. Surface: Smooth.

*Peduncle.*—Length: Long, averaging about 8 cm. Surface: Glandular. Color: Yellow-Green Group 144A overlaid with irregular patch of Greyed-Red Group 178B. Strength: Normal.

Bloom:

*Size.*—Large. Average open diameter is about 9.2 cm.

*Borne.*—In irregular compound corymb clusters of about six blooms.

*Form.*—When first open: Cupped. Permanence: Retains its form to the end, very outer petals curl back.

*Petalage.*—Number of petals under normal conditions: 80–90.

*Color.*—The upper sides of the petals are Red Group 38D. The reverse sides of the petals are Red Group 37C with Red Group 38B around margin.

*Variegations.*—None.

*Discoloration.*—The general tonality at the end of the first day is Red Group 38D. At the end of the third day: Red Group 56C.

*Fragrance.*—Strong, myrrh.

Petals:

*Texture.*—Smooth.

*Size.*—Width: 2.8 cm. Length: 3.7 cm.

*Surface.*—Smooth.

*Shape.*—Obovate (inner petals); obdeltoid (outer petals). Margin: Mainly notched (outer petals); mainly entire (inner petals). Apex Shape: Obcordate (outer petals); obtuse (inner petals). Base Shape: Cuneate. Form: Incurved, tips of very outer petals slightly recurved.

*Arrangement.*—Imbricated.

*Petaloids.*—Number: 5. Color: Anther: Yellow-Orange Group 17C. Filament: Yellow Group 13C. Petal: Red Group 39C. Length: Anther 2 mm; Filament: 8–12 mm; Petal: 10 mm.

*Persistence.*—Petals drop off cleanly before drying.

*Lastingness.*—On the plant: Fair (about 5 days). As a cut flower: Fair (about 5 days).

Reproductive parts:

*Stamens.*—Number: 55–60. Length: 8–9 mm. Anthers: Length: 2 mm. Color: Yellow-Orange Group 17A. Arrangement: Regular around styles, mixed with petaloids. Filaments: Color: Yellow Group 9A. Length: 6–7 mm. Pollen: Color: Yellow-Orange Group 17A.

*Pistils.*—Number: 30–35. Length: 8 mm. Styles: Color: Yellow-Green Group 145D with Red Group 47B concentrated under stigma. Length: 7 mm. Stigmas: Color: Yellow-Orange Group 20A. Length: 1 mm.

*Hips.*—None observed.

PLANT

*Form.*—Shrub.

*Growth.*—Vigorous, upright, bushy.

*Age of maturity.*—Two years.

*Mature plant.*—Height: 1.2 m. Width: 1.2 m.

*Rootstock.*—'Dr. Huey' in the USA. *Rosa dumetorum* 'Laxa' for the observed plants in the U.K.

Foliage: Number of leaflets on normal mid-stem leaves: 5 or 7. (including terminal leaflet).

*Size.*—Medium. About 15.9 cm long×11.4 cm wide.

*Quantity.*—Normal. Average number leaves per flowering stem: 10.

*Color.*—New foliage: Upper side: Yellow-Green Group 146A. Lower side: Yellow-Green Group 146C overlaid with Greyed-Red Group 178B. Old foliage: Upper side: Green Group 137A. Lower side: Yellow-Green Group 146B.

Leaflets:

*Size.*—About 6.1 cm long×4.6 cm wide.

*Shape.*—Ovate.

*Base shape.*—Rounded.

*Apex shape.*—Acuminate.

*Texture.*—Leathery, glossy.

*Edge.*—Serrated.

*Serrations.*—Single, small.

*Petiole.*—Color: Yellow-Green Group 146B upper surface and Yellow-Green Group 144A lower surface. Length: 3 cm. Width: 2 mm. Surface texture: Smooth.

*Petiole rachis.*—Color: Yellow-Green Group N144D. Underside: With prickles.

*Stipules.*—Length: 1.5–1.7 cm, serrated. Color: Yellow-Green Group 144D.

*Auricle shape.*—Subulate. Length: 5 mm. Width: 2 mm, tapering to a point. Color: Yellow-Green Group 144D.

*Disease resistance.*—Resistant to powdery and downy mildew, blackspot and rust in normal growing conditions.

*Pest resistance.*—Not tested.

*Vein color.*—Yellow-Green Group N144D.

*Venation pattern.*—Reticulate.

Wood:

*New wood.*—Color: Yellow-Green Group 152A overlaid with Greyed-Red Group 178B. Bark: Smooth.

*Old wood.*—Color: Yellow-Green Group 146B. Bark: Smooth.

Stems:

*Mature stem.*—Length: 35 cm. Diameter: 6 mm.

*Internode distance.*—7 cm. The above measurements are all variable, depending on growing conditions in a season.

Prickles:

*Quantity.*—On main canes from base: Ordinary, 6 per 5 cm stem length. On laterals from main canes: Few, 2 per 5 cm per stem length.

*Form.*—Concave, curved inward.

*Length.*—9 mm.

*Color when young.*—Orange-Red Group N34A.

*Color when mature.*—Greyed-Yellow Group 161B.

Small prickles:

*Quantity.*—On main stalks: None. On laterals: None.

Winter hardiness: Not tested.

I claim:

1. A new and distinct variety of shrub rose plant substantially as herein shown and described, characterized particularly by its medium sized, cupped rosettes of pure mid-pink blossoms; having a very strong myrrh fragrance; and its tall, slightly arching growth with dark, glossy foliage.

* * * * *

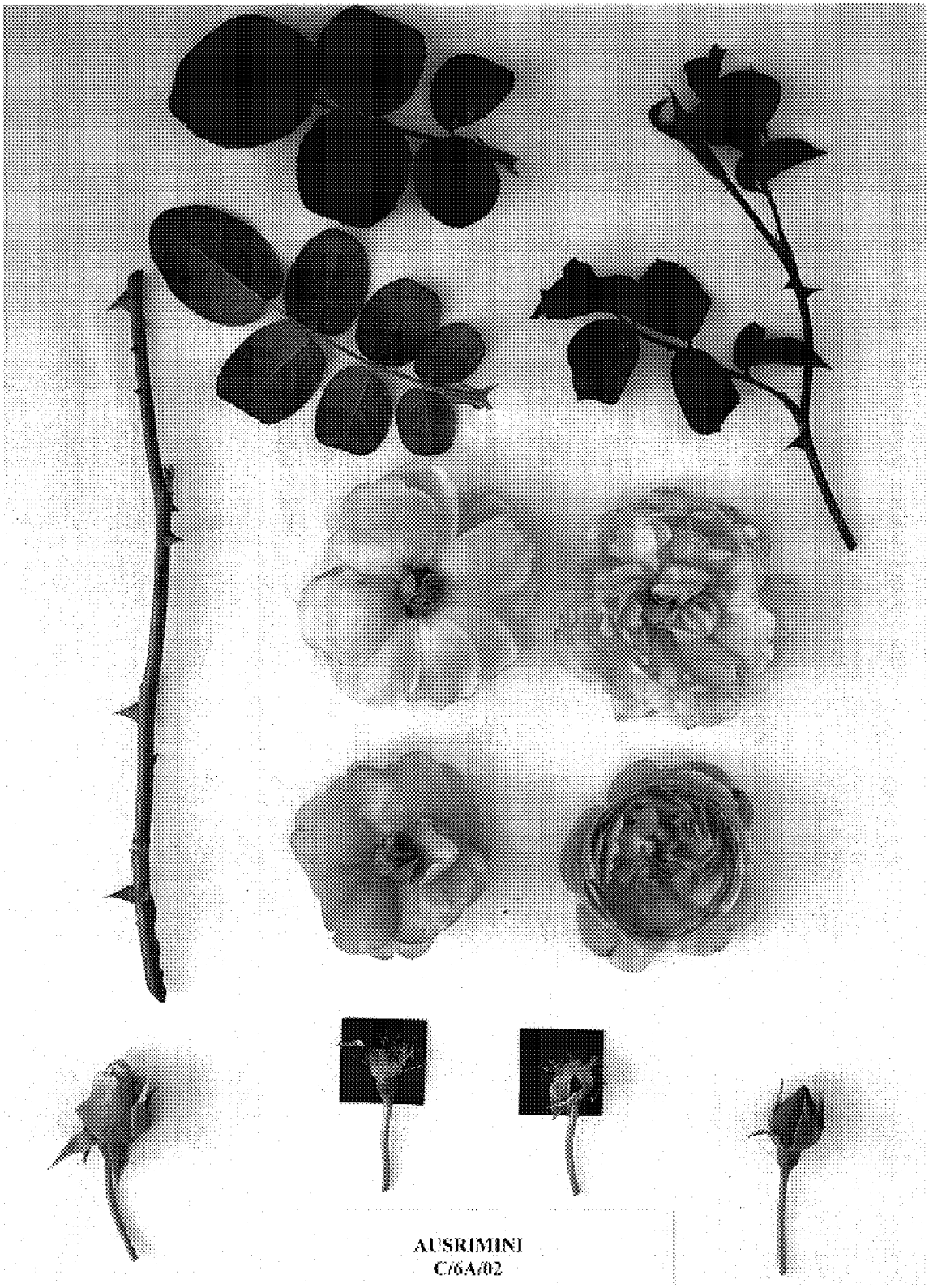
AUSRIMINI
C/6A/02